(12) United States Patent
Choudhary et al.

(10) Patent No.: US 6,437,191 B1
(45) Date of Patent: Aug. 20, 2002

(54) PROCESS FOR THE ACYLATION OF AROMATIC COMPOUNDS USING A REUSABLE SOLID CATALYST COMPRISING INDIUM HALIDE

(75) Inventors: Vasant Ramchandra Choudhary; Suman Kumar Jana; Nilesh Sudhir Patil, all of Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/724,500

(22) Filed: Nov. 28, 2000

(51) Int. Cl.$^7$ ................................................ C07C 45/46
(52) U.S. Cl. ...................... 568/319; 568/309; 568/322; 568/323
(58) Field of Search .................. 568/309, 312, 568/314, 316, 323, 322; 502/224; 585/467

(56) References Cited

U.S. PATENT DOCUMENTS 6,180,557 B1 * 1/2001 Choudhary et al. ......... 502/224

* cited by examiner

Primary Examiner—Sreeni Padmanabhan
(74) Attorney, Agent, or Firm—Ladas & Parry

(57) ABSTRACT

A process for the liquid phase acylation of aromatic compounds by acyl halides to corresponding acylated aromatic compounds, using a reusable solid catalyst comprising indium halide represented by a formula:

$$M_xIn_{1-x}Ay(a)/s$$

wherein,

S is a porous catalyst support selected from clays, zeolites and zeolite-like materials;

M is a metallic chemical element(s) selected from the group consisting of Ga (gallium), Fe (iron), Zn (zinc), Ti (titanium) and a mixture of two or more thereof;

In is a metallic chemical element, indium;

A is a non-metallic chemical element selected from the group consisting of Cl (chlorine), Br (bromine), I (iodine), F (fluorine) and a mixture of two or more thereof;

is mole fraction of M in the metallic elements in the range from 0.01 to 0.99;

y is the number of A atoms required to satisfy the valence requirement of $M_xIn_{1-x}$; and a is the loading of $M_xIn_{1-x}$ A on the support, S, in the range from 0.05 mmol.g$_{-1}$ to 5.0 mmol.g$^{-1}$, at the following reaction conditions: weight ratio of catalyst to acylating agent in the range trom about 0.05 to about 5.0; mole ratio of aromatic compound to acylating agent in the range from about 0.1 to about 100; weight ratio of non-aqueous solvent to aromatic compound in the range from zero to about 100; reaction temperature in the range from about 10° C. to about 300° C.; pressure at least 1.0 atm; gas hourly space velocity of inert gas bubbled through the liquid reaction mixture in the range from zero h$^{-1}$ to about 5000 h$^{-1}$; and reaction period in the range from about 0.02 h to about 100 h, is provided.

16 Claims, No Drawings

PROCESS FOR THE ACYLATION OF AROMATIC COMPOUNDS USING A REUSABLE SOLID CATALYST COMPRISING INDIUM HALIDE

FILED OF THE INVENTION

The present invention relates to a process for the liquid phase acylation of aromatic compounds using a solid catalyst comprising indium halide. This invention particularly relates to a process for the acylation of aromatic compounds for preparing acylated aromatic compounds using a reusable solid catalyst comprising indium halide.

The process for this invention could be used for the preparation of acylated aromatic compounds, which are fine chemicals and/or used as intermediates in the preparation of fine chemicals or speciality chemicals in dyes and pharmaceutical industries and other chemical industries.

BACKGROUND OF THE INVENTION

Prior art discloses both homogeneous and heterogeneous liquid phase processes based on Friedel-Crafts type reactions for the preparation of acylated aromatic compounds.

Friedel-Crafts Type Acylation Reactions Catalyzed by Homogeneous Catalysts

The Friedel-Crafts type acylation of aromatic compounds by various acylating agents using homogeneous Lewis Acid catalysts, such as $AlCl_3$, $BF_3$, $ZnCl_2$ and other metal chlorides and protonic acid catalysts, such as $H_2SO_4$, $H_3PO_4$, HF, etc., are well known in the prior art (ref G. A. Olah, in Friedel-Crafts and related reactions: vol. III, Acylation and related reactions, Wiley-Interscience Publ., New York, 1964).

U.S. Pat. No. (5,476,970 (1995)) of Rains et al., discloses a homogeneous liquid phase process for the acylation of $R_1,R_2C_6H_4$ by $R_3R_4C_6H_3COCl$, wherein $R_1$, $R_2$, $R_3$ and $R_4$ are chemical groups, using $FeCl_3$ catalyst at high pressures. French patent (FR 2768728 (1999)) and (FR 2768729 (1999)) of Baudry et al., discloses liquid phase homogeneous process for the benzoylation of anisole by benzoyl chloride using rare earth halides or uranyl halide.

Japanese Patent (JP 08277241, A2 (1996)) of Kunikata discloses a liquid phase process for the acylation of phenol by phenyl acetyl chloride using a homogeneous $AlCl_3$ catalyst. Japanese Patent (JP 09059205, A2 (1997)) of Oono discloses the use of AlCl, as a homogeneous catalyst for the acylation of toluene with acetyl chloride at high pressure.

Japanese Patent (JP 2000086570, A2 (2000)) of Shoji et al., discloses a homogeneous liquid phase process for the acylation of toluene by acetyl fluoride using HF-BF, as a catalyst.

The main disadvantages of the Friedel-Crafts type acylation processes based on the use of above mentioned homogeneous acid catalysts are as follows:

1) The separation and recovery of the dissolved acid catalysts from the liquid reaction mixture is difficult.

2) The disposal of the used acid catalysts creates environmental pollution.

3) The homogeneous acid catalysts also pose several other problems such as high toxicity, corrosion, spent acid disposal and use of more than the, stoichiometric amount.

Friedel-Crafts Type Acylation Reactions Catalyzed by Heterogeneous Solid Catalysts A few liquid phase processes for the acylation of aromatic compounds by acyl halides using solid catalysts are also known in the prior art.

Japanese Patent (JP 01089894, A2 (1995)) of Myata et al., discloses a liquid phase process for the acylation of toluene with benzoyl chloride using ammonium chloride treated H-beta zeolite catalyst under reflux for $3h$ to get para-acylated toluene with 28% yield. French Patent (FR 2745287, A1 (1997)) of Barbier et al. discloses the liquid phase acylation of anisole by benzoyl acloride under reflux using neodymium chloride deposited on montmorillonite K-10 clay.

Vincent et al., (ref Tetrahedron Lett. 35, 1994, 2601) discloses that H-ZSM-5 zeolite can catalyze the acylation by benzoyl chloride of phenol and anisole but not the acylation with benzoyl chloride of benzene and naphthalene at 120° C. for 5 h.

Acylation of aromatic compound involves electrophilic substitution of H from the aromatic nucleus of the aromatic compound. It is well known in the prior art that the electrophilic substitution is favoured by the presence of electron donating groups. such as OH. alkyl, alkoxy, phenoxy. amine, alkyl amine, SH etc., in the aromatic compound. Whereas the electrophilic substitution is inhibited by the presence of electron withdrawing groups such halo, nitro, cyano, carboxy, aldehyde, etc., in the aromatic compound (ef. G.A.Olah, in Friedel-Crafts and related reactions, Wiley-Interscience Publ., New York, 1963).

Although some limitations of the homogeneous acid catalyzed process are overcome in the prior art heterogeneous solid catalyzed processes described above, the acylating activity of the solid acid catalysts used in the prior art processes is low, particularly for acylating aromatic compounds not containing electron donating groups, such as benzene, naphthalene, etc. Both the prior art homogeneous and heterogeneous acid catalysts are highly moisture sensitive, and hence demand moisture-free or thoroughly dried reactants, solvents and catalyst for the Friedel-Crafts type acylation processes. In presence of moisture in the reaction mixture homogeneous and heterogeneous catalysts show poor activity in the Friedel-Crafts processes. Hence, there is a great practical need for finding more efficient and also moisture insensitive solid catalyst for the acylation of aromatic compounds.

The main object of this invention is to provide a liquid phase process for the acylation of aromatic compounds, including those not containing electron donating groups using novel solid catalyst which has high activity not only when the aromatic ring activating groups (i.e. electron donating groups such as alkyl, alkoxy, hydroxy, phenoxy, etc.) are present in the aromatic ring to be acylated but also when the ring activating group in the aromatic ring to be acylated is absent, so that the reaction temperature is low and or time for completing the reaction is shot.

Another object of this invention is to provide a liquid phase process for the acylation of aromatic compounds, using a novel solid catalyst which is easily separable and reusable in the process.

Yet another object of this invention is to provide a solid catalyzed liquid phase process for the acylation of aromatic compounds event in the presence of moisture in the reacon mixture.

SUMMARY OF THE INVENTION

Accordingly the present invention provides a process for the liquid phase acylation of an aromatic compound (1) of the formula $(R_1,R_2R_3R_4)$—D—H by an acylating agent (II) of the formula $(R_5R_6R_7)$—Y—Z to produce corresponding acylated aromatic compound (III) of the formula $((R_1,$ $R_2R_3R_4$)—D—Y—($R_5R_6R_7$), wherein D is an aromatic nucleus selected from side aromatic ring containing 6 C-atoms and 1 H-atom or fused two aromatic rings containing 10 C-atoms and 3 H-atoms and three fused aromatic rings containing 14 C-atoms and 5 H-atoms; $R_1$, $R_2$, $R_3$ and $R_4$ are chemical groups attached to the aromatic nucleus, D; Y is a nucleus of the acylating agent selected from the group consisting of C—CO, $C_nH_{2n-2}$CO, $C_6H_2$—CO, $C_6H_2C_nH_{2n}$—CO and $C_6H_2C_nH_{n2-1}$(X)-CO; $R_5$, $R_6$ and $R_7$ are chemical groups attached to the nucleus of acylating agent Y; Z is selected from Cl, Br and I; X is a halogen group; and n is an integer $\geq 1.0$, using a solid catalyst (IV), comprising indium halide, represented by a formula $M_xIn_{1-x}Ay(a)/S$ wherein S is a porous catalyst support selected from clays, zeolites and zeolite-like materials; M is a metallic chemical element selected from the group consisting of Ga, Fe, Zn, Ti ox a mixture of two or more thereof; A is a non-metallic chemical element selected from the group consisting of Cl, Br, I, F and a mixture of two or more thereof, x is a mole fraction of M and is in the range from 0.01 to 0.99; y is the number of A atoms required to satisfy the valence requirement of $M_xIn_{1-x}$; and a is a loading of $M_xIn_{1-x}A$ on the support S and is in the range of from 0.05 mmol.$g^{-1}$ to 5.0 mmol.$g^{-1}$; said process comprising:

i) pretreating said catalyst (IV) under vacuum or flow of an inert gas selected from nitrogen, helium and argon at a temperature in the range from 50° C. to 300° C. for a period sufficient to remove adsorbed moisture from the catalyst;

ii) contacting a liquid reaction mixture comprising said aromatic compound (I) and said acylating agent (II) in the presence or absence of a non-aqueous. solvent with the pretreated catalyst in a stirred batch reactor fitted with a reflux condenser under vigorous stirring, in the presence or absence of an inert gas bubbling through the reaction mixture, at following reaction conditions: weight ratio of catalyst (IV) to acylating agent (II) in the range from about 0.05 to about 5.0, mole ratio of aromatic compound to acylating agent in the range from about 0.1 to about 100, weight ratio of non-aqueous solvent to aromatic compound in the range from zero to about 100, reaction temperature in the range from about 10° C. to about 300° C., pressure at least 1.0 atm, gas hourly space velocity of inert gas bubbled through the liquid reaction mixture in the range from zero $h^{-1}$ to about 5000 $h^{-1}$ and reaction period in the range from about 0.02 h to about 100 h;

iii) cooling the reaction mixture to a temperature about 30° C., removing said catalyst from the reaction mixture by filtration and then separating the reaction products from the reaction mixture, and optionally washing the used catalyst by non-aqueous solvent or aromatic substrate; and iv) reusing the used catalyst for subsequent reaction batch.

In another embodiment of the invention, each of the $R_1$, $R_2$, $R_3$ and $R_4$ chemical groups is selected from the group consisting of hydrogen, alkane, olefinic, phenyl, alkoxy, phenoxy, hydroxyl, aldehydic, ketonic, amine, amide, thio and sulphonic acid groups.

In another embodiment of the invention, Z is Cl or Br.

In a further embodiment of the invention, each of the $R_5$, $R_6$, and $R_7$ chemical groups is selected from hydrogen, alkane, olefinic, phenyl, halogen, nitro and cyano groups.

In another embodiment of the invention, the weight ratio of catalyst to acylating agent is in the range from about 0.1 to 1.0.

In another embodiment of the invention, the mole ratio of aromatic compound to acylating agent is in the range from 0.5 to 20.

In another embodiment of the invention, the weight ratio of non-aqueous solvent to aromatic compound is in the range from zero to 20.

In another embodiment of the invention, the reaction temperature is in to range from 20° C. to 200° C.

In another embodiment of the invention, the reaction period is preferably in the range from 0.1 h to 20 h.

In another embodiment of the invention, the space velocity of inert gas in the range from 50 $h^{-1}$ to 500 $h^{-1}$.

In another embodiment of the invention, M is selected from Ga Fe and a fixture thereof In another embodiment of the invention, wherein A is Cl.

In another embodiment of the invention, the loading of metal halides a, on the support in the catalyst is in the range from 0.3 mmol.$g^{-1}$ to 3.0 mmol.$g^{-1}$.

In another embodiment of the invention, the catalyst support S is selected from mesoporous MCM-41 and montmorillonite clay.

In another embodiment of the invention, the non-aqueous solvent is selected from the group consisting of dichloroethane, nitrobenzene, nitromethane, chlorobenzene, n-hexane, -heptane and n-octane.

In a further embodiment of the invention, the non-aqueous solvents is selected form dichloroethane and nitrobenzene.

The main finding of this invention is that the said catalyst shows high activity in the acylation of aromatic compounds not only when the electron donating group, which is aromatic ring activating group, is present in the aromatic ring to be acylated, but also when the electron donating group is absent in the aromatic ring to be acylated, and hence the reaction temperature is low and/or the time required for completing the reactions is short.

Other important finding of this invention is that said solid catalyst can be separated easily and reused repeatedly in the process. Another important finding of this invention is that the acylation of aromatic compound over said catalyst occurs with high reaction rates even in the presence of moisture in the reaction mixture.

DETAILED DESCRIPTION OF THE INVENTION

Accordingly, this invention provides a liquid phase process for the acylation of an aromatic compound represented by a formula:

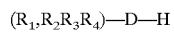

by an acylating agent (II) represented by a formula;

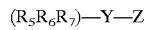

to produce corresponding acylated aromatic compound (III) represented by a formula:

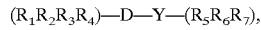

wherein, D is an aromatic nucleus such as single aromatic ring containing 6 C-atoms and I H-atom or fused two aromatic rings containing 10 C-atoms and 3-H atoms or three fused aromatic rings containing 14 C-atoms and 5 H-atoms;

$R_1$, $R_2$, $R_3$ and $R_4$ are chemical groups attached to the aromatic nucleus, D;

Y, which is a nucleus of the acylating agent, is selected from C—CO, $C_nH_{2n-2}$CO, $C_6H_2$—CO, $C_6H_2C_nH_{2n}$—

CO and $C_6H_2C_nH_{2n-1}(X)$—CO; $R_5$, $R_6$ and $R_7$ are chemical groups attached to the nucleus of acylating agent, Y;

Z is a chemical group selected from Cl, Br and I;
X is a halogen group;
H is hydrogen;
C is carbon;
O is oxygen;
Cl is chlorine;
Br is bromine;
I is iodine; and
n is an integer having a value equal to or greater than 1.0, using a solid catalyst (IV), comprising indium halide, represented by a formula:

$$M_xIn_{1-x}Ay(a)/S$$

wherein,
S is a porous catalyst support selected from clays, zeolites and zeolite-like materials;
M is a metallic chemical element(s) selected from Ga(gallium), Fe (iron), Zn(zinc), Ti (titanium) or a mixture of two or more thereof;
In is a metallic chemical element, indium;
A is a non-metallic chemical element selected from Cl(chlorine), Br (bromine ), I(iodine), F(fluorine) or a mixture of two or more thereof;
x is a mole fraction of M in the metallic elements in the range from 0.01 to 0.99;
y is the number of A atoms required to satisfy the valance requirement of $M_xIn_{1-x}$; and
a is the loading of $M_xIn_{1-x}$ A on the support, S, in the range from 0.05 mmol.$g^{-1}$ to 5.0 mmol.$g^{-1}$; the process comprises:
  i) pretreating said catalyst (IV) under vacuum or flow of an inert gas selected from nitrogen, helium or argon at a temperature in the range from 50° C. to 300° C. for a period sufficient to remove adsorbed moisture from the catalyst;
  ii) contacting a liquid reaction mixture comprising said aromatic compound (I) and said acylating agent (II) in the presence or absence of a non-aqueous solvent with the pretreated catalyst in a stirred batch reactor fitted with a reflux condenser under vigorous stirring, in the presence or absence of an inert gas bubbling through the reaction mixture, at following reaction conditions: weight ratio of catalyst (IV) to acylating agent (II) in the range from about 0.05 to about 5.0. mole ratio of aromatic compound to acylating agent in the range from about 0.1 to about 100, weight ratio of non-aqueous solvent to aromatic compound in the rage from zero to about 100, reaction temperature in the range from about 10° C. to about 300° C., pressure at least 1.0 atm, gas hourly space velocity of inert gas bubbled through the liquid reaction mixture in the range from zero $h^{-1}$ to about 5000 $h^{-1}$ and reaction period in the range from about 0.02 to about 100 h;
  iii) cooling the reaction mixture to a temperature about 30° C., removing said catalyst from the reaction mixture by filtration and then separating the reaction products from the reaction mixture, and optionally washing the used catalyst by non-aqueous solvent or aromatic substrate; and
  iv) reusing the used catalyst for subsequent reaction batch.

Each of $R_1$, $R_2$, $R_3$ and $R_4$ chemical groups may be selected from H or $CnH_{2n+1}$ or $C_mH_{2m-1}$ or $C_6H_5$ or $C_nH_{2n}C_6H_5$ or OH or $OC_nH_{2n+1}$ or $OC_6H_5$ or halogen or $NO_2$ or $NH_2$ or $NHC_nH_{2n+1}$ or $N(C_nH_{2n+1})_2$ or $NHCOC_nH_{2n+1}$ or $NHCOC_6H_5$ or CN or CHO or COOH or $COOC_nH_{2n+1}$ or $COC_nH_{2n+1}$ or $SO_3H$ or $SO_3C_nH_{2n-1}$ or SH or alkyl mercapto group or aryl mercapto group and each of $R_5$, $R_6$ and $R_7$ chemical groups may be H or $CH_3$ or $C_2H_5$ or OH or $OCH_3$ or $OC_2H_3$ or $NO_2$, wherein n and m are integers greater than or equal to 1 and 2, respectively, and C, H, N, O and S are chemical elements—carbon, hydrogen. nitrogen, oxygen and sulfur, respectively, In the process of the present invention, the preferred reaction temperature may be between 20° C. and 200° C.; the preferred reaction period may be between 0.1 h and 20 h; the preferred gas hourly space velocity of inert gas bubbled through the reaction mixture may be between 50 $h^{-1}$ and 500 $h^{-1}$; the preferred weight ratio of catalyst to acylating agent may be between 0.1 and 1.0; the preferred mole ratio of aromatic compound to acylating agent may be between 0.5 and 20; the preferred weight ratio of non-aqueous solvent to aromatic compound may be between zero and 20; each of the preferred $R_1$, $R_2$ $R_3$ and $R_4$ chemical groups may be selected from hydrogen (H), alkane ($C_nH_{2n+1}$), olefinic ($C_mH_{2m-1}$), phenyl ($C_6H_5$), alkoxy ($OC_nH_{2-1}$), phenoxy ($OC_6H_5$), hydroxyl (OH), aldehydic (CHO), ketonic (RCO), amine ($NH_2$), amide ($CONH_2$), thio (SH) and sulfonic acid ($HSO_3$) groups, wherein n and m are integers having value $\geq 1$ and $\geq 2$, respectively, each of the preferred $R_5$, $R_6$ and $R_7$, chemical groups may be selected from hydrogen. alkane, olefinic. phenyl. halogen (Cl or Br or X or F), nitro (NO2) and cyano (CN) groups; the preferred chemical group Z may be selected from Cl of Br; the preferred metallic element, M, in the catalyst is Ga or Fe or a mixture of the two; the preferred non-metallic element, A, in the catalyst is Cl; the preferred loading of metal halides, a, on the support in the catalyst is in the range from 0.3 mmol.g–1 to 3.0 mmol.g–1; and the preferred catalyst support, S, is mesoporous MCM-41 or montmorillonite clay.

Zeolites are crystalline aluminosilicates containing well defined channels or pores of uniform diameter. A large number of microporous (pore size $\leq 1.0$ nm) zeolites, such as X, Y, mordenite, L, beta, ZSM-5, ZSM-8, ZSM-11, etc., and mesoporous (pore size=1.5 nm to 50 nm) zeolites, such as M41S type material, e.g. MCM-41, are known in the prior-art (ref Breck in Zeolite Molecular Sieves, Wiley-Interscience Publ., New York, 1974; Beck and Co-workers. J.Am. Chem.Soc., vol. 114, page 1083 4, year 1992; Nature (London) vol.359, page 710, year 1992). A number of cation exchange natural and synthetic clays having layered silicate structure, for example montmorillonite, kaoline, and the like, are known in the prior art ref. R. A. Schoonheydt "Clays: from two to three dimensions" in Studies in Surface Science and Catalysis, vol. 58, page 201–238, 1991; and K. Ohtsuka, Chem. Mater., vol. 9, page 2039–2051, year 1997).

The process of this invention can be carried out in a stirred batch reactor, fitted with a reflux condenser and arrangement for bubbling inert gas through the reaction fixture, known in the prior art for carrying out liquid phase reactions.

In the process of this invention, the main products formed are said acylated aromatic compound and a by-product HX, wherein H=hydrogen and X=halogen, depending upon the acylating agent used.

In the process of this invention, aromatic compound and acylating agent are reactants and are converted partly or completely to said products.

The process of this invention may be carried out with or without using a solvent, such as dichloroethane, nitrobenzene, nitromethane, chlorobenzene, n-hexane, -heptane, n-octane or other non-aqueous solvents. In the process of this invention, the role of solvent, is to dissolve solid reactant or reactants and thereby to facilitate the reaction between the aromatic compound and the acylating agent. However, solvent way not be used in the process of this invention when both the reactants are liquids at said reaction conditions. Normally, said solvent is not converted in the process of this invention.

In the process of this invention, the role of inert gas bubbling contiguously through the reaction mixture is to remove continuously said by-product from the reaction mixture so that the reverse reaction is avoided or minimized and the time required for completing the reaction is shortened. In the absence of bubbled inert gas, the reaction can still take place but with incomplete conversion and/or requiring longer period.

In the process of this invention, the role of the reflux condenser fitted with the reactor is to condense reactants and/or solvent, and to return them back to the reaction mixture and allow the inert gas, which is continuously bubbling through the reaction mixture, along with said by-product to escape from the reaction mixture.

Said pre-treatment to said catalyst in step-I of the process of present intention is required for removing the traces of moisture from the catalyst.

In the process of this invention, the reaction pressure above atmospheric pressure may be used to allow the reaction to be carried out at temperature higher than the normal boiling point of the reactants and/or solvent, by increasing the boiling point of said reactants and/or solvent with increasing the reaction pressure.

Said catalyst, used in the process of this invention, is heterogeneous with respect to the reaction mixture and can be removed from the reaction mixture simply by filtration and the removed catalyst, after washing with solvent or said liquid aromatic compound, which is to be acylated, can be reused in the said process.

The role of said catalyst is to activate both the reactants—aromatic compound and acylating agent and thereby to increase rate of the reaction.

By the process of this invention, benzene (which does not contain any electron donating group) can also be benzoylated with benzoyl chloride to benzophcnone at 80° C. with 91% conversion of benzoyl chloride for a reaction period of 1.5 h.

The present invention is described with respect to the following Examples illustrating the process of this invention for the acylation of aromatic compounds using said solid catalyst comprising indium halide. However, these examples are provided for illustrative purposes only and are not to be construed as limitations on scope ot the process of this invention.

DEFINITION OF TERMS USED IN THE EXAMPLES

Conversion of reactant (%)=mole % of the reactant converted in the process. All the ratios of aromatic compounds to acylating agent are mole ratios. All the solid catalyst to acylating agent and solvent to aromatic compound ratios are weight ratios.

The flow rates of inert gas is measured at 0° C. and 1 atm pressure. Gas hourly space velocity (GHSV) is volume of gas, measured at 0° C. and 1 atm pressure, passed through unit volume of the liquid reaction mixture per hour.

Ac and Aa represent aromatic compound to be acylated and acylating agent, respectively and y is a number of halogen atoms required to satisfy the valance requirement of the metallic elements present in the catalyst of this invention.

EXAMPLES 1–16

These examples illustrate the process of this invention for the liquid phase acylation of aromatic compounds by different acylating agents to corresponding acylated aromatic compounds using a reusable solid catalyst of this invention.

The process of this invention was carried out by contacting the solid catalyst with a 15 cm3 liquid reaction mixture containing aromatic compound to be acylated and an acylating agent with or without non-aqueous solvent, in a stirred batch reactor (capacity: 25 cm3) and fitted with a reflux condenser, mercury thermometer dipped in the reaction mixture and an ink tube for passing gas through the reaction mixture, under vigorous stirring, while bubbling moire-free inert gas through the reaction mixture at the reaction conditions given in Table 1 and measuring quantitatively the gaseous hydrogen halide evolved during the reaction by absorbing it in aqueous NaOH solution by a simple acid-base titration using phenolphthalein indicator, and then cooling the reaction mixture to room temperature (30° C.) and analyzing the product and unconverted reactants present in the reaction mixture, after separating the solid catalyst from it by filtration, by a gas chromatograph with a thermal conductivity detector, using a SE 30 column and hydrogen as carrier gas.

The solid catalysts used in these examples were prepared as follows:

The $Ga_{0.1}In_{0.9}Cl_y$ (1.2 mmol $g^{-1}$)/Si—MCM-41 catalyst was prepared by depositing 1.2 mmol anhydrous $GaCl_3$ (Aldrich) and 10.8 mmol anhydrous InCl3 (Aldrich) from their acetonitrilc solution on 10 g Si—MCM-41 by incipient wetness technique followed by drying at 120° C. for 8 h.

The $Ga_{0.95}In_{0.05}Cl_y$ (1.3 mmol $g^{-1}$)/Si—MCM-41 catalyst was prepared by depositing 12.35 mmol anhydrous $GaCl_3$ (Aldrich) and 0.65 mmol anhydrous $InCl_3$ (Aldrich) from their acetonitrile solution on 10 g Si—MCM-41 by incipient wetness technique followed by drying at 120° C. for 8 h.

The $Ga_{0.051}In_{0.95}Cl_y$ (1.2 mmol $g^{-1}$)/Mont. K-10 catalyst was prepared by depositing 0.6 mmol anhydrous $GaCl_3$ (Aldrich) and 11.4 mmol anhydrous $InCl_3$ (Aldrich) from their acetonitrile solution on 10 g Mont. K-1–0 by incipient wetness technique followed by drying at 120° C. for 8 h.

The $Ga_{0.5}In_{0.5}Cl_y$ (1.1 mmol $g^{-1}$)/Si—MCM-41 catalyst was prepared by depositing 5.5 mmol anhydrous $GaCl_3$ (Aldrich) and 5.5 mmol anhydrous $InCl_3$ (Aldrich) from their acetonitrile solution on 10 g Si—MCM-41 by incipient wetness technique followed by drying at 120° C. for 8 h.

The $Ga_{0.99}In_{0.01}Cl_y$ (0.6 mmol $g^{-1}$)/Kaoline catalyst was prepared by depositing 5.94 mmol anhydrous $GaCl_3$ (Aldrich) and 0.06 mmol anhydrous $InCl_3$ (Aldrich) from their acetonitrile solution on 10 g Kaoline by incipient wetness technique followed by drying at 120° C. for 8 h.

The $Fe_{0.03}In_{0.97}Cl_y$ (1.2 mmol $g^{-1}$)/Mont. KSF catalyst was prepared by depositing 0.36 mmol anhydrous $FeCl_3$ (Aldrich) and 11.64 mmol anhydrous $InCl_3$ (Aldrich) from their acetonitrile solution on 10 g Mont. KSF by incipient wetness technique followed by drying at 120° C. for 8 h.

The $Zn_{0.9}In_{0.1}Cl_y$ (2.5 mmol $g^{-1}$)/Mont. K-10 catalyst was prepared by depositing 22.5 mmol anhydrous $ZnCl_2$ (Aldrich) and 2.5 mmol anhydrous $InCl_3$ (Aldrich) from their acetonitrile solution on 10 g Mont. K-10 by incipient wetness technique followed by drying at 120° C. for 8 h.

The $Zn_{0.1}Ga_{0.1}In_{0.8}Cl_y$ (1.1 mmol $g^{-1}$)/H-beta catalyst was prepared by depositing 1.1 mmol anhydrous $ZnCl_2$ (Aldrich), 1.1 mmol anhydrous $GaCl_3$ (Aldrich) and 8.8 mmol anhydrous $InCl_3$ (Aldrich) from their acetonitrile solution on 10 g H-beta zeolite by incipient wetness technique followed by drying at 120° C. for 8 h.

The $Ga0.2In_{0.8}Cl_y$ (0.3 mmol $g^{-1}$)/H-mordenite catalyst was prepared by depositing 0.6 mmol anhydrous $GaCl_3$ (Aldrich) and 2.4 mmol anhydrous $InCl_3$ (Aldrich) from their acetonitrile solution on 10 g H-mordenite by incipient wetness technique followed by drying at 120° C. for 8 h.

The $Fe_{0.08}In_{0.92}Cl_y$ (0.9 mmol $g^{-1}$)/Si—MCM-41 catalyst was prepared by depositing 0.72 mmol anhydrous $FeCl_3$ (Aldrich) and 8.28 mmol anhydrous $InCl_3$ (Aldrich) from their acetonitrile solution on 10 g Si—MCM-41 by incipient wetness technique followed by drying at 120° C. for 8 h.

The $Ga_{0.3}In_{0.7}Cl_y$ (1.1 mmol $g^{-1}$)/Mont. K-10 catalyst was prepared by depositing 3.3 mmol anhydrous $GaCl_3$ (Aldrich) and 7.7 mmol anhydrous $InCl_3$ (Aldrich) from their acetonitrile solution on 10 g Mont. K-10 by incipient wetness technique followed by drying at 120° C. for 8 h.

The Mont K-10 (montmorillonite K-10), Mont KSF (montmorillonite KSF) and kaolin clays were obtained from Aldrich Chemicals Co, USA. The Si—MCM-41 mesoporous crystalline material was prepared by the procedure given by Mokaya et. al., [Ref. Mokaya, R. and Jones, W., Chemical Communication, year 1997, pp. 2185–2186]. H-mordenite was obtained from Norton Co., USA. The H-beta zeolite was prepared by the method used by Singh and Bhattacharya (ref. Catalysis Letters Vol. 32, page 327, year 1995).

Results of the acylation of aromatic compound by the process of this invention at different process conditions and using different aromatic compounds, acylating agents and catalysts of this invention are presented as Examples 1–16 in Table-1.

In Example-16, the benzene saturated with water was prepared by string 20 ml pure benzene with 2 ml water at 30° C. fox 5 h and removing the water by a separating funnel.

TABLE 1

Results of the Acylation of Different Aromatic Compounds

| Example No. | Example 1 | Example 2 | Example 3 | Example 4 |
|---|---|---|---|---|
| Catalyst | $Ga_{0.1}In_{0.9}Cl_y$(1.2 mmol.$g^{-1}$)/ Si-MCM41 | Same as that used in Example 1 | Same as that used in Example 1 | Same as that used in Example 1 |
| Reactant: | | | | |
| Aromatic compound (Ac) | Benzene | Toluene | 2-methyl naphthalene | Anisole |
| Acylating agent (Aa) | Benxoyl chloride | Benzoyl chloride | Acetyl chloride | Phenyl acetyl chloride |
| Reaction Conditions: | | | | |
| Solvent | Nil | Nil | Dichloroethane | Nil |
| Ac/Aa mole ratio | 17.0 | 17.0 | 1.5 | 15.0 |
| Solvent/Aa mole ratio | 0.0 | 0.0 | 13.0 | 0.0 |
| Catalyst/Aa weight ratio | 0.33 | 0.33 | 0.33 | 0.33 |
| Temperature (° C.) | 80 | 110 | 50 | 154 |
| Pressure (atm) | 1.0 | 1.0 | 1.0 | 1.0 |
| GHSV of $N_2$ ($h^{-1}$) | 99 | 99 | 99 | 99 |
| Reaction time (h) | 1.5 | 1.0 | 3.0 | 0.5 |
| Conversion of acylating agent (%) | 90.9 | 95.6 | 96.3 | 97.9 |
| Main product of reaction | $C_6H_5COC_6H_5$ | $CH_3C_6H_4COC_6H_3$ | $CH_3C_{10}H_6COCH_3$ | $(CH_3O)C_6H_4COCH_2C_6H_5$ |
| By-product of reaction | HCl | HBr | HCl | HCl |
| Example No. | Example 5 | Example 6 | Example 7 | Example 8 |
| Catalyst | Same as that used in Example 1 | $Ga_{0.95}In_{0.05}Cl_y$ (1.3 mmol.$g^{-1}$)/ Si-MCM41 | $Ga_{0.05}In_{0.95}Cl_y$ (1.2 mmol.$g^{-1}$)/ Si-MCM41 | $Ga_{0.5}In_{0.05}Cl_y$ (1.1 mmol.$g^{-1}$)/ Si-MCM41 |
| Reactant: | | | | |
| Aromatic compound (Ac) | 2-methoxy naphthalene | Benzene | Benzene | p-Xylene |
| Acylating agent (Aa) | Benxoyl chloride | Benzoyl chloride | Benzoyl chloride | Benzoyl chloride |
| Reaction Conditions: | | | | |
| Solvent | Dichloroethane | Nil | Nil | Nil |
| Ac/Aa mole ratio | 2.0 | 16.9 | 15.7 | 15.0 |
| Solvent/Aa mole ratio | 20 | 0.0 | 0.0 | 0.0 |
| Catalyst/Aa weight ratio | 0.33 | 0.3.3 | 0.50 | 0.33 |
| Temperature (° C.) | 80 | 82 | 85 | 154 |
| Prcssure (atm) | 1.0 | 1.1 | 1.6 | 1.0 |
| GHSV of $N_2$ ($h^{-1}$) | 99 | 205 | 95 | 99 |
| Reaction time (h) | 0.75 | 2.5 | 3.5 | 0.5 |
| Conversion of acylating agent (%) | 98.8 | 80.5 | 95.6 | 97.9 |
| Main product of reaction | $(CH_3O)C_{10}H_6COCH_2C_6H_5$ | $C_6H_5COC_6H_5$ | $C_6H_5COC_6H_5$ | $(CH_3)_2C_6H_3COC_6H_5$ |
| By-product of reaction | HCl | HBr | HCl | HCl |

TABLE 1-continued

Results of the Acylation of Different Aromatic Compounds

| Example No. | Example 9 | Example 10 | Example 11 | Example 12 |
|---|---|---|---|---|
| Catalyst | $Ga_{0.99}In_{0.01}Cl_y$ (0.6 mmol.g$^{-1}$)/ Kaoline | $Fe_{0.03}In_{0.97}Cl_y$ (1.2 mmol.g$^{-1}$)/ Mont. KSF | $Zn_{0.9}In_{0.1}Cl_y$ (2.5 mmol.g$^{-1}$)/ Mont. K-10 | $Zn_{0.1}Ga_{0.1}In_{0.8}Cl_y$ (1.1 mmol.g$^{-1}$)/ H-beta |
| Reactant: | | | | |
| Aromatic compound (Ac) | Benzene | Naphthalene | Toluene | Benzene |
| Acylating agent (Aa) | Benzoyl chloride | Propionyl bromide | Benzoyl Bromide | Benzoyl chloride |
| Reaction Conditions: | | | | |
| Solvent | Nil | Dichloroethane | Nil | Nil |
| Ac/Aa mole ratio | 13.0 | 1.1 | 13.5 | 9.5 |
| Solvent/Aa mole ratio | 0.0 | 13.0 | 0.0 | 0.0 |
| Catalyst/Aa weight ratio | 0.33 | 0.6 | 0.3 | 0.33 |
| Temperature (° C.) | 87 | 81 | 115 | 81 |
| Pressure (atm) | 1.3 | 1.1 | 1.3 | 1.1 |
| GHSV of $N_2$ (h$^{-1}$) | 125 | 55 | 175 | 125 |
| Reaction time (h) | 15 | 1.3 | 3.7 | 6.5 |
| Conversion of acylating agent (%) | 91.3 | 80.5 | 98.9 | 94.3 |
| Main product of reaction | $C_6H_5COC_6H_5$ | $C_{10}H_7COC_3H_7$ | $CH_3C_6H_4COC_6H_5$ | $C_6H_5COC_6H_5$ |
| By-product of reaction | HCl | HBr | HCl | HCl |

| Example No. | Example 13 | Example 14 | Example 15 | Example 16 |
|---|---|---|---|---|
| Catalyst | $Ga_{0.2}In_{0.8}Cl_y$ (0.3 mmol.g$^{-1}$)/ H-mordenite | $Fe_{0.08}In_{0.92}Cl_y$ (0.9 mmol.g$^{-1}$)/ Si-MCM-41 | $Ga_{0.3}In_{0.7}Cl_y$ (1.1 mmol.g$^{-1}$)/ Mont. K-10 | Same as that used in Example 1 |
| Reactant: | | | | |
| Aromatic compound (Ac) | Benzene | Mesitylene | Naphthalene | Benzene saturated with water |
| Acylating agent (Aa) | Benzoyl chloride | Benzoyl bromide | Butyryl chloride | Benzoyl chloride |
| Reaction Conditions: | | | | |
| Solvent | Nil | Nil | Dichlorocthane | Nil |
| Ac/Aa mole ratio | 5.0 | 7.0 | 0.5 | 15.0 |
| Solvent/Aa mole ratio | 0.0 | 0.0 | 1.5 | 0.0 |
| Catalyst/Aa weight ratio | 0.9 | 0.4 | 1.0 | 0.33 |
| Temperature (° C.) | 85 | 175 | 80 | 154 |
| Pressure (atm) | 1.2 | 1.4 | 1.3 | 1.0 |
| GHSV of $N_2$ (h$^{-1}$) | 93 | 120 | 0.0 | 99 |
| Reaction time (h) | 14 | 3.0 | 10 | 0.5 |
| Conversion of acylating agent (%) | 97.1 | 97.5 | 49.9 | 96.1 |
| Main product of reaction | $C_6H_5COC_6H_5$ | $(CH_3)_3C_6H_2COC_6H_5$ | $C_{10}H_7COC_4H_9$ | $C_6H_5COC_6H_5$ |
| By-product of reaction | HCl | HBr | HCl | HCl |

EXAMPLES 17–20

These examples illustrate the process of this invention, showing reusabilitn of the catalyst used in the earlier examples. for the acylation of aromatic compounds by the process of this invention.

The process of this invention for the liquid phase acylation of aromatic compounds using the catalyst which was already used in the earlier examples was carricd out using the reactor and the procedure same as that described in Example 1 except that the used catalyst in the earlier example was washed before its use with the aromatic substrate or the solvent, which is to be used in the subsequent example.

The results showing the reusability of the catalyst of this invention in the process of this invention are presented in Table 2.

The observations and conclusions from the results in Examples 1–20 are summarized as follows:

1. The catalyst of this invention shows very high activity for the acylation of different aromatic compounds, even when there are no election donating group present in the aromatic compound.

2. The catalyst of this invention shows very high activity for the acylation of aromatic compounds even in the presence of moisture in the reaction mixture.

3. The catalyst of this invention is reusable in the process of this invention.

TABLE 2

Results showing reusability of the catalyst of this invention for the process of this invention

| Example No. | Example 17 | Example 18 | Example 19 | Example 20 |
|---|---|---|---|---|
| Catalyst | The catalyst after its use in Example 1 | The catalyst after its use in Example 17 | The catalyst after its use in Example 15 | The catalyst after its use in Example 10 |
| Reactant: | | | | |
| Aromatic compound (Ac) | Toluene | Anisole | Benzene | Naphthalene |
| Acylating agent (Aa) | Benzoyl chloride | Butyryl chloride | Benzoyl chloride | Propionyl chloride |
| Reaction Conditions: | | | | |
| Solvent | Nil | Nil | Nil | Nitromethane |
| Ac/Aa mole ratio | 17.9 | 16.5 | 17.1 | 2.0 |
| Solvent/Aa mole ratio | 0.0 | 0.0 | 0.0 | 15.0 |
| Catalyst/Aa weight ratio | 0.3 | 0.25 | 0.5 | 0.5 |
| Temperature (° C.) | 110 | 163 | 82 | 103 |
| Pressure (atm) | 1.0 | 1.3 | 1.2 | 1.2 |
| GHSV of $N_2$ ($h^{-1}$) | 105 | 95 | 97 | 91 |
| Reaction time (h) | 1.4 | 1.0 | 2.0 | 2.0 |
| Conversion of acylating agent (%) | 97.9 | 98.5 | 98.4 | 98.6 |
| Main product of reaction | $CH_3C_6H_4COC_6H_5$ | $(CH_3O)C_6H_4COC_4H_9$ | $C_6H_5COC_6H_5$ | $CH_{10}H_7COC_3H_7$ |
| By-product of reaction | HCl | HCl | HBr | HBr |

The novel features and main advantages of the process of this invention over the prior art processes for the acylation of aromatic compound are as follows:

1) The process of this invention has a number of advantages over the earlier homogeneous acid catalyzed processes for the acylation of aromatic compounds, as follows:

In the process of this invention,
i) the catalyst used is solid catalyst and hence it can be separated from the reaction products simply by filtration,
ii) the separated catalysts can be reused in the process of this invention, and
iii) also the catalyst is non corrosive.

Hence all the serious problems associated with homogeneous catalyst used in the earlier homogeneous processes for the preparation of acylated aromatic compounds overcome in the process of this invention.

2) The process of this invention has also a number of advantages over the prior art processes based on the use of solid acid catalyst for the acylation of aromatic compounds, as follows:

i) The activity of the said catalyst used in the process of this invention is much higher and hence the time required for completing the reaction is much shorter.
ii) The catalyst of this invention can be reused repeatedly in the process and the reused catalyst shows very high activity in the process even after its repeated to in the process.
iii) The process of the present invention can be used for acylating both small and large size aromatic compounds with both small and large size acylating agents to produce the corresponding acylated aromatic compounds.
iv) In the process of this invention, when inert gas is bubbled through the reaction mixture continuously, said by-product formed in the reaction is removed continuously, and thereby the reverse acylation reaction is avoided or minimized, thus requiring shorter time for completing the reaction.
v) By the process of this invention, even the acylation of benzene or naphthallene, which does not contain any aromatic ring activating electron donating group such as alkyld alkoxy, hydroxy etc., group, is rapid at mild reaction conditions and hence the reaction is accomplished at a much shorter reaction period than that required in the prior art processes.
vi) In the process of this invention, by using the solid catalvst comprising indium halide, a rapid acylation of aromatic compound is possible even when the reaction mixture contains moisture; the catalyst is not deactivated due to the presence of moisture in the reaction mixture. Hence, unlike the prior art homogeneous and solid acid catalysts, the catalyst of this invention does not demand moisture-free conditions to be active in the process and hence there is no need to remove traces of moisture from the reactants and solvent used in the process, and thereby the process of this invention becomes more economical.

We claim:

1. A process for the liquid phase acylation of an aromatic compound (I) of the formula $(R_1R_2R_3R_4)$—D—H by an acylating agent (II) of the formula $(R_5R_6R_7)$—Y—Z to produce corresponding acylated aromatic compound (III) of the formula $((R_1R_2R_3R_4)$—D—Y—$(R_5R_6R_7)$, wherein D is an aromatic nucleus selected from single aromatic ring containing 6 C-atoms and 1 H-atom or fused two aromatic rings containing 10 C-atoms and 3 H-atoms and three fused aromatic rigs containing 14 C-atoms and 5 H-atoms;

$R_1$, $R_2$, $R_3$ and $R_4$ are chemical groups attached to the aromatic nucleus, D;

Y is a nucleus of the acylating agent selected from the group consisting of C—CO, $C_nH_{2n-2}CO$, $C_6H_2$—CO, $C_6H_2C_nH_{2n}$—CO and $C_6H_2C_nH_{2n-1}(X)$—CO; $R_5$, $R_6$ and $R_7$ are chemical groups attached to the nucleus of acylating agent Y;

Z is selected from Cl, Br and I; X is a halogen group; and n is an interger $\geq 1.0$, using a solid catalyst (IV), comprising indium halide, represented by a formula

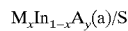
$M_xIn_{1-x}A_y(a)/S$ wherein
S is a porous catalyst support selected from clays, zeolites and zeolite-like materials;

M is a metallic chemical element selected from the group consisting of Ga, Fe, Zn, Ti or a mixture of two or more thereof;

A is a non-metallic chemical element selected from the group consisting of Cl, Br, I, F and a mixture of two or more thereof;

x is a mole fraction of M and is in the range from 0.01 to 0.99;

y is the number of A atoms required to satisfy the valence requirement of $M_xIn_{1-x}$; and a is the loading of $M_xIn_{1-x}A$ on the support S and is in the range of from 0.05 mmol.g$^{-1}$ to 5.0 mmol.g$^{-1}$;

said process comprising v) pretreating said catalyst (IV) under vacuum or flow of an inert gas select from nitrogen, helium and argon at a temperature in the range from 50° C. to 300° C. for a period sufficient to remove adsorbed moisture from the catalyst;

vi) contacting a liquid reaction mixture comprising said aromatic compound (I) and said acylating agent (II) in the presence or absence of a non-aqueous solvent with the pretreated catalyst in a stirred batch reactor fitted with a reflux condenser under vigorous stirring, in the presence or absence of an inert gas bubbling through the reaction mixture, at following reaction conditions: weight ratio of catalyst (IV) to acylating agent (II) in the range from about 0.05 to about 5.0, mole ratio of aromatic compound to acylating agent in the range from about 0.1 to about 100, weight ratio of non-aqueous solvent to aromatic compound in the range from zero to about 100, reaction temperature in the range from about 10° C. to about 300° C., pressure at least 1.0 atm, gas hourly space velocity of inert gas bubbled through the liquid reaction mixture in the range from zero h$^{-1}$ to about 5000 h$^{-1}$ and reaction period in the range from about 0.02 h to about 100 h;

vii) cooling the reaction mixture to a temperature about 30° C., removing said reaction mixture by filtration and then separating the reaction products from the reaction mixture, and optionally washing the used catalyst by non-aqueous solvent or aromatic substrate; and viii) reusing the used catalyst for subsequent reaction batch.

2. A process as claimed in claim 1, wherein each of the $R_1$, $R_2$, $R_3$ and $R_4$ chemical groups is selected from the group consisting of hydrogen, alkane, olefinic, phenyl, alkoxy, phenoxy, hydroxyl, aldehydic, ketonic, amine, amide, thio and sulphonic acid groups.

3. A process as claimed in claim 1 wherein Z is Cl or Br.

4. A process as claimed in claim 1 wherein each of the $R_5$, $R_6$ and $R_7$ chemical groups is selected from hydrogen, alkane, olefinic, phenyl, halogen, nitro and cyano groups.

5. A process as claimed in claim 1 wherein the weight ratio of catalyst to acylating agent is in the range from about 0.1 to 1.0.

6. A process as claimed in claim 1 wherein the mole ratio of aromatic compound to acylating agent is in the range from 0.5 to 20.

7. A process as claimed in claim 1 wherein the weight ratio of non-aqueous solvent to aromatic compound is in the range from zero to 20.

8. A process as claimed in claim 1 wherein the reaction temperature is in the range from 20° C. to 200° C.

9. A process as claimed in claim 1 wherein the reaction period is in the range from 0.1 h to 20 h.

10. A process as claimed in claim 1 wherein the space velocity of inert gas is in the range from 50 h$^{-1}$ to 500 h$^{-1}$.

11. A process as claimed in claim 1 wherein M is selected from Ga, Fe and a mixture thereof.

12. A process as claimed in claim 1 wherein A is Cl.

13. A process as claimed in claim 1 wherein the loading of metal halides a, on the support in the catalyst is in the range from 0.3 mmol.g$^{-1}$ to 3.0 mmol.g$^{-1}$.

14. A process as claimed in claim 1 wherein the catalyst support S is selected from mesoporous MCM-41 and montmorillonite clay.

15. A process as claimed in claim 1 wherein the non-aqueous solvent is selected from the group consisting of dichloroethane, nitrobenzene, nitromethane, chlorobenzene, n-hexane, n-heptane and n-octane.

16. A process as claimed in claim 15 wherein the non-aqueous solvent is selected form dichioroethane and nitrobenzene.

* * * * *